(12) United States Patent  (10) Patent No.: US 7,951,204 B2
Chambat et al.  (45) Date of Patent: *May 31, 2011

(54) KNEE PROSTHESIS WITH A ROTATIONAL PLATE

(75) Inventors: Pierre Chambat, Ste Foy les Lyon (FR); Gérard Deschamps, Givry (FR); Thierry Judet, Ville d'Avray (FR); Philippe Neyret, Caluire (FR)

(73) Assignee: Tornier SAS, St. Ismier (FR)

( * ) Notice: Subject to any disclaimer, the term of this patent is extended or adjusted under 35 U.S.C. 154(b) by 884 days.

This patent is subject to a terminal disclaimer.

(21) Appl. No.: 11/143,742

(22) Filed: Jun. 3, 2005

(65) Prior Publication Data

US 2006/0015185 A1    Jan. 19, 2006

Related U.S. Application Data

(63) Continuation of application No. 09/832,874, filed on Apr. 12, 2001, now abandoned, which is a continuation of application No. 09/158,791, filed on Sep. 23, 1998, now Pat. No. 6,299,646.

(30) Foreign Application Priority Data

Sep. 23, 1997  (FR) .................................... 97 12042

(51) Int. Cl.
    *A61F 2/38*       (2006.01)
(52) U.S. Cl. ................................................... 623/20.33
(58) Field of Classification Search ..... 623/20.14–20.36
    See application file for complete search history.

(56) References Cited

U.S. PATENT DOCUMENTS

| 4,714,474 A | 12/1987 | Brooks, Jr. et al. |
| 4,728,332 A | 3/1988  | Albrektsson |
| 4,950,297 A | 8/1990  | Elloy et al. |
| 5,171,289 A | 12/1992 | Tornier |
| 5,282,868 A | 2/1994  | Bahler |
| 5,314,485 A | 5/1994  | Judet |
| 5,326,359 A | 7/1994  | Oudard |
| 5,344,460 A | 9/1994  | Turanyi et al. |
| 5,358,526 A | 10/1994 | Tornier |

(Continued)

FOREIGN PATENT DOCUMENTS

EP    A 0 346 183    12/1989

(Continued)

OTHER PUBLICATIONS

Restriction Requirement Office Action mailed Mar. 17, 2000 from USPTO for U.S. Appl. No. 09/158,791, Issued Patent No. 6,299,646.

(Continued)

*Primary Examiner* — Bruce E Snow
(74) *Attorney, Agent, or Firm* — Faegre & Benson LLP

(57) ABSTRACT

The knee prosthesis with rotary plate comprises a metal base (2) and a tibia plate (3) which are equipped with guide means (22, 22', 22'', 26, 29, 5, 6, 5', 9, 50, 51, 52, 13, 15, 18; 34, 34', 34'', 35, 37, 7, 8, 10, 12, 53, 54, 55, 10', 17) defining a center of rotation (C,C') which may be offset from that of the tibia bone axis (YY'), so as to allow the tibia plate (3) to slide in rotation over the said base, the said guide means being positioned a certain distance away from the center of rotation (C, C').

17 Claims, 11 Drawing Sheets

U.S. PATENT DOCUMENTS

| | | | |
|---|---|---|---|
| 5,387,240 A * | 2/1995 | Pottenger et al. | 623/20.29 |
| 5,405,399 A | 4/1995 | Tornier | |
| 5,429,639 A | 7/1995 | Judet | |
| 5,458,650 A | 10/1995 | Carrett et al. | |
| 5,505,731 A | 4/1996 | Tornier | |
| 5,591,168 A | 1/1997 | Judet et al. | |
| 5,658,342 A | 8/1997 | Draganich et al. | |
| 5,662,651 A | 9/1997 | Tornier et al. | |
| 5,676,702 A | 10/1997 | Ratron | |
| 5,683,468 A | 11/1997 | Pappas | |
| 5,702,447 A | 12/1997 | Walch et al. | |
| 5,702,457 A | 12/1997 | Walch et al. | |
| 5,702,478 A | 12/1997 | Tornier | |
| 5,766,256 A | 6/1998 | Oudard et al. | |
| 5,824,106 A | 10/1998 | Fournol | |
| 5,871,543 A | 2/1999 | Hofmann | |
| 5,879,394 A | 3/1999 | Ashby et al. | |
| 5,879,395 A | 3/1999 | Tornier et al. | |
| 5,951,603 A * | 9/1999 | O'Neil et al. | 623/20.33 |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,206,925 B1 | 3/2001 | Tornier | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,379,387 B1 | 4/2002 | Tornier | |
| 6,454,809 B1 | 9/2002 | Tornier | |
| 6,488,712 B1 | 12/2002 | Tornier et al. | |
| 6,540,770 B1 | 4/2003 | Tornier et al. | |
| 6,582,469 B1 | 6/2003 | Tornier | |
| 6,599,295 B1 | 7/2003 | Tornier et al. | |
| 6,626,946 B1 | 9/2003 | Walch et al. | |
| 6,761,740 B2 | 7/2004 | Tornier | |
| 6,767,368 B2 | 7/2004 | Tornier | |
| 6,802,864 B2 | 10/2004 | Tornier | |
| 6,824,567 B2 | 11/2004 | Tornier et al. | |
| 6,890,357 B2 | 5/2005 | Tornier | |
| 6,969,406 B2 | 11/2005 | Tornier | |
| 7,033,396 B2 | 4/2006 | Tornier | |
| 2003/0009170 A1 | 1/2003 | Tornier | |
| 2003/0009171 A1 | 1/2003 | Tornier | |
| 2003/0028198 A1 | 2/2003 | Tornier et al. | |
| 2004/0134821 A1 | 7/2004 | Tornier | |
| 2004/0210220 A1 | 10/2004 | Tornier | |
| 2004/0215200 A1 | 10/2004 | Tornier et al. | |
| 2004/0230197 A1 | 11/2004 | Tornier et al. | |
| 2005/0049709 A1 | 3/2005 | Tornier | |
| 2005/0055102 A1 | 3/2005 | Tornier et al. | |
| 2005/0165490 A1 | 7/2005 | Tornier | |
| 2005/0203536 A1 | 9/2005 | Laffargue et al. | |
| 2005/0278030 A1 | 12/2005 | Tornier et al. | |
| 2005/0278031 A1 | 12/2005 | Tornier et al. | |
| 2005/0278032 A1 | 12/2005 | Tornier et al. | |
| 2005/0278033 A1 | 12/2005 | Tornier et al. | |
| 2005/0288791 A1 | 12/2005 | Tornier et al. | |
| 2006/0173457 A1 | 8/2006 | Tornier | |
| 2006/0235538 A1 | 10/2006 | Rochetin et al. | |
| 2007/0043265 A1 | 2/2007 | Rochetin | |
| 2007/0173947 A1 | 7/2007 | Ratron et al. | |
| 2007/0179628 A1 | 8/2007 | Rochetin | |
| 2007/0270718 A1 | 11/2007 | Rochetin et al. | |

FOREIGN PATENT DOCUMENTS

| | | |
|---|---|---|
| EP | 0634156 | 1/1995 |
| FR | 2707871 | 1/1995 |
| FR | 2 735 017 | 12/1996 |
| GB | 2061730 | 5/1981 |
| GB | 2 312 377 A | 10/1997 |

OTHER PUBLICATIONS

Non-Final Office Action mailed Apr. 24, 2000 from USPTO for U.S. Appl. No. 09/158,791, Issued Patent No. 6,299,646.

Final Office Action mailed Oct. 12, 2000 from USPTO for U.S. Appl. No. 09/158,791, Issued Patent No. 6,299,646.

Advisory Office Action mailed Jan. 9, 2001 from USPTO for U.S. Appl. No. 09/158,791, Issued Patent No. 6,299,646.

Advisory Office Action mailed Feb. 20, 2001 from USPTO for U.S. Appl. No. 09/158,791, Issued Patent No. 6,299,646.

Notice of Allowance mailed Apr. 18, 2001 from USPTO for U.S. Appl. No. 09/158,791, Issued Patent No. 6,299,646.

Rochetin, et al., U.S. Appl. No. 11/401,415, filed Apr. 11, 2006, file wrapper.

Rochetin, U.S. Appl. No. 11/194,452, filed Aug. 2, 2005, file wrapper.

Ratron, et al., U.S. Appl. No. 11/626,735, filed Jan. 24, 2007, file wrapper.

Rochetin, U.S. Appl. No. 11/670,274, filed Feb. 1, 2007, file wrapper.

* cited by examiner

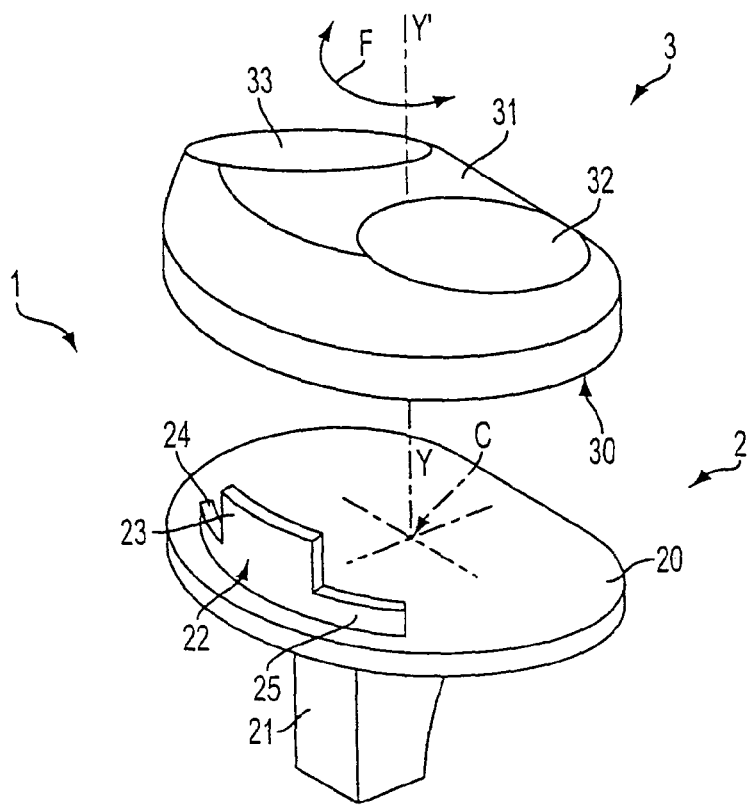
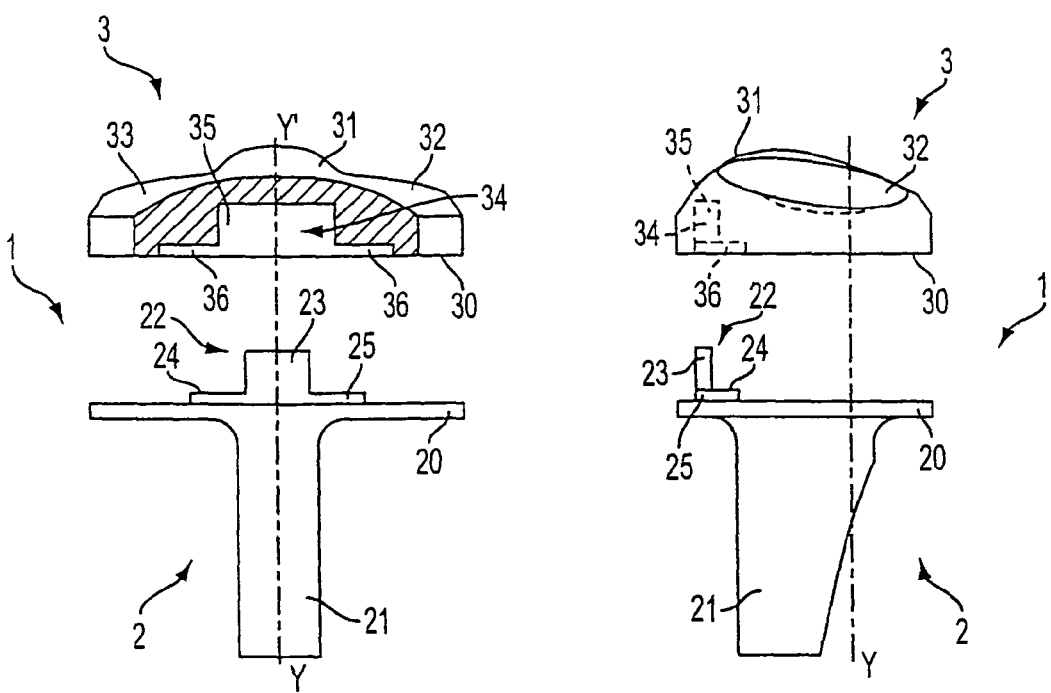
FIG. 1
FIG. 2
FIG. 3

KNEE PROSTHESIS WITH A ROTATIONAL PLATE

CROSS-REFERENCE TO RELATED APPLICATIONS

This application is a Continuation of application Ser. No. 09/832,874, filed Apr. 12, 2001, now abandoned, in the name of the same inventors which is a Continuation of application Ser. No. 09/158,791, filed Sep. 23, 1998, now U.S. Pat. No. 6,299,646, issued Oct. 9, 2001, also in the name of the same inventors. The entire contents of the prior applications is incorporated herein by reference. This application also claims priority benefits of French Patent Application FR 97 12042, filed Sep. 23, 1997.

BACKGROUND OF THE INVENTION

1. Field of the Invention

The present invention relates to a knee prosthesis and more specifically to the device for assembling its tibia plate, which is made of plastic, on its metal base anchored beforehand into the tibia bone tissue.

2. Discussion of the Background Information

Knee prostheses which comprise a plastic tibia part which is free to rotate about the tibia bone axis with respect to the metal base secured to the tibia are known.

This freedom of rotation is generally achieved via a male shaft integral with the plastic tibia part which engages with a bore made in the metal base.

Furthermore, this freedom of rotation may be achieved by a male shaft secured to the metal base which engages with a bore made in the plastic tibia part.

These connecting devices have certain drawbacks, namely the difficulty of inserting the plastic tibia plate once the metal base is in place on the tibia. These drawbacks are exacerbated when the posterior cruciate ligament is being kept, as this restricts access to the upper part of the tibia.

Furthermore, it is observed that the center of rotation is necessarily positioned at a point of the device or [sic] the bore can be made, that is to say in a part or [sic] there is enough material to make the said bore. This arrangement of the center of rotation is not strictly anatomical.

It can be seen that the volume generated by the tibia bone axis may prevent a posterior cutout from being made in the plastic tibia plate or in the metal base to allow the posterior cruciate ligament to be kept.

Knee prostheses which comprise a plastic tibia plate which slides freely over the flat surface of the metal base, and the movement of which is limited by one or more cylindrical studs integral with the base communicating with spaces made in the plastic plate are also known.

This type of prosthesis has the drawback of not physically embodying an axis of rotation.

It is these drawbacks which the present invention sets out more particularly to overcome.

SUMMARY OF THE INVENTION

The knee prosthesis according to the present invention is intended to provide a plastic tibia plate which has a degree of freedom in rotation with respect to the metal base.

The knee prosthesis in accordance with the present invention comprises a metal base and a tibia plate which are equipped with guide mechanism defining a center of rotation which may be offset from that of the tibia bone axis, so as to allow the tibia plated to slide in rotation over the base, the guide mechanism being positioned a certain distance away from the center of rotation.

The knee prosthesis has guide mechanism which utilizes at least one upstand in the shape of an arc of a circle secured to the metal base and of a housing with the same radius of curvature made in the plastic tibia plate to allow the latter to slide in rotation about the center of rotation of the upstand.

The knee prosthesis according to the present invention comprises guide mechanism which utilizes an upstand in the shape of an arc of a circle, which upstand is positioned in the anterior part of the metal base and oriented in a substantially medio-lateral direction.

The knee prosthesis according to the present invention comprises additional guide mechanism which is positioned on or near to the center of rotation of the tibia plate on the metal base.

The knee prosthesis according to the present invention comprises additional guide mechanism which is secured to a device making it possible to prevent the tibia plate from lifting from the metal base.

The knee prosthesis in accordance with the present invention comprises guide mechanism which utilizes at least two pegs set out in an arc of a circle and defining a center of rotation, and of a housing of the same radius of curvature formed in the tibia plate.

The knee prosthesis according to the present invention comprises a metal base which comprises an upstand in the shape of an arc of a circle having a central part secured to lateral edges which are not as tall as the said central part, while the tibia plate comprises, on its lower face, a housing in the shape of an arc of a circle.

The knee prosthesis according to the present invention comprises an upstand which has a center of rotation which is borne by the tibia bone vertical axis, while the upstand is a certain distance away from its center of rotation.

The knee prosthesis according to the present invention comprises an upstand which has a center of rotation which is offset from the tibia bone vertical axis, while the upstand is a certain distance away from its center of rotation.

The knee prosthesis according to the present invention comprises a metal base which has two upstands in the shape of an arc of a circle, of constant height and having one and the same center of rotation, while the tibia plate comprises two housings in the shape of an arc of a circle.

The knee prosthesis according to the present invention comprises upstands which are set out opposite one another, and have one and the same center of rotation.

The knee prosthesis according to the present invention comprises a metal base which has, opposite the upstand, a retaining peg borne by a center of rotation so as to engage with a cutout formed in the tibia plate to prevent the latter from lifting off the base as the plate slides in rotation about its center of rotation.

The knee prosthesis according to the present invention comprises a retaining peg which utilizes a cylindrical pin integral with a head which has a larger diameter than the pin so that the head engages with inclined faces made in the cutout.

The knee prosthesis according to the present invention comprises a metal base which has, opposite the upstand, a centering peg borne by the center of rotation so as to engage with a blind hole formed in the tibia plate to guide the latter with respect to the base as the plate slides in rotation about its center of rotation.

The knee prosthesis according to the present invention comprises a metal base and a tibia plate which respectively comprise a cutout through which the posterior cruciate ligament can pass.

The knee prosthesis according to the present invention comprises a metal base which has two upstands in the shape of an arc of a circle curved in the same direction and centered about the same center of rotation, while the tibia plate comprises housings intended to receive the upstands respectively, so as to allow the plate to slide in rotation about the center of rotation.

The knee prosthesis according to the present invention comprises an upstand which is integral with a flange which engages in a slot in the housing to prevent the tibia plate from lifting off the metal base as the plate slides in rotation about the center of rotation.

The knee prosthesis according to the present invention comprises a metal base which comprises two upstands in the shape of an arc of a circle in opposite directions and centered about the same center of rotation, while the tibia plate comprises an element and a housing which are intended to receive the upstands respectively to allow the plate to slide in rotation about the center of rotation.

The knee prosthesis according to the present invention comprises an upstand which is set out on the external periphery of the horizontal disk of the metal base so as to engage with a peripheral recess in the tibia plate.

The knee prosthesis according to the present invention comprises an upstand which is offset from the center of rotation and comprises a flange which snap-fastens into the housing in the tibia plate to, on the one hand, guide the plate as it slides in rotation about its center and, on the other hand, retain the plate so that it does not lift off the metal base.

The knee prosthesis according to the present invention comprises a metal base which comprises a peripheral upstand in the shape of an arc of a circle integral with a flange directed toward the tibia bone vertical axis and a housing set out in the region of the center of rotation, while the tibia plate has, on its external periphery, a recess in which there is formed a horizontal slot intended to receive the flange of the upstand and, on its lower face, a stub which engages with the housing.

The knee prosthesis according to the present invention comprises a metal base which comprises three peripheral upstands extending vertically above the horizontal disk, while the tibia plate has, on its external periphery, three recesses intended to receive the upstands respectively to allow the plate to be guided as it slides in rotation about the center of rotation.

The knee prosthesis according to the present invention comprises pegs which are set out in an arc of a circle about a center of rotation, while the tibia plate has a housing intended to receive the pegs.

The knee prosthesis according to the present invention comprises pegs which have a center of rotation which is borne by the tibia bone vertical axis, while the peg is a certain distance away from its center of rotation.

The knee prosthesis according to the present invention comprises pegs which have a center of rotation which is offset from the tibia bone vertical axis, while the peg is a certain distance away from its center of rotation.

The knee prosthesis according to the present invention comprises a metal base which comprises at least one upstand or peg which engages with a housing of the tibia plate so that the plate can slide in rotation over the metal base only within the limit set by the difference in size between the upstand or peg and the corresponding housing.

The knee prosthesis according to the present invention has a rotational travel between the tibia plate and the metal base which is reduced to zero when the dimensions of the housing are made so as to engage without clearance with the upstand.

The knee prosthesis according to the present invention has a short height of the guide mechanism and of their anterior positioning on the metal base which allows the tibia plate to be mounted on the base via a strictly anterior approach, the plate requiring upward clearance only by the height of the guide mechanism.

BRIEF DESCRIPTION OF THE DRAWINGS

The description which will follow with reference to the appended drawings, given by way of non-limiting examples, will allow a good understanding of the invention, its features and the advantages it is likely to afford:

FIG. 1 is an exploded perspective view illustrating the knee prosthesis according to the present invention.

FIGS. 2 and 3 are side views showing the knee prosthesis before the plastic tibia plate is fitted on the metal base.

DETAILED DESCRIPTION OF THE PRESENT INVENTION

Figure 4:
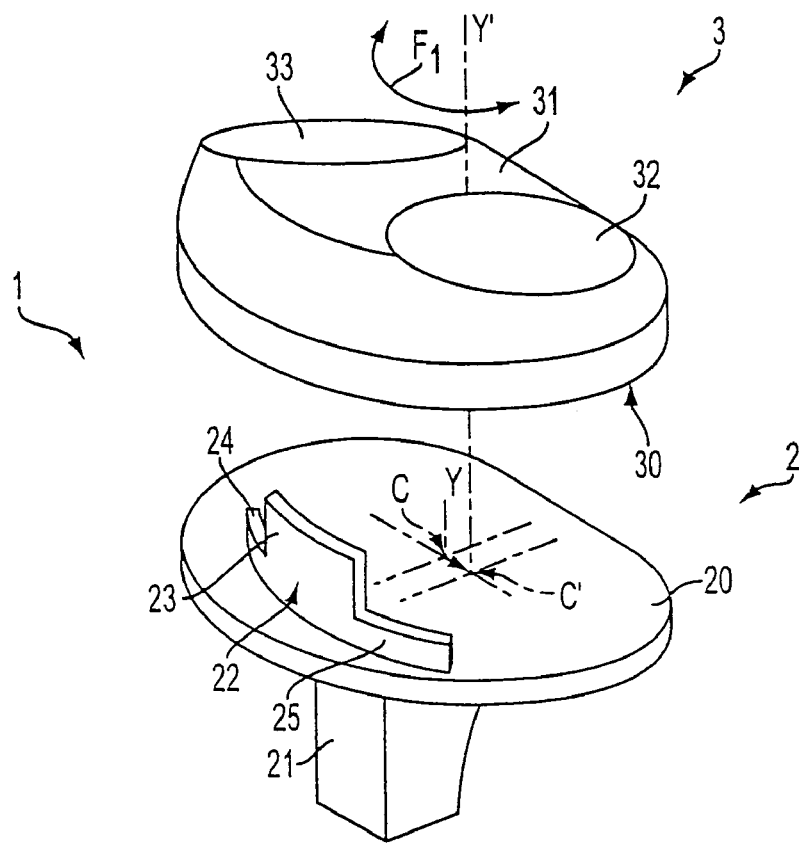
FIGS. 4 and 5 are views depicting a first alternative form of the knee prosthesis according to the invention.

FIGS. 1 to 3 show a knee prosthesis 1 comprising a metal base 2 and a tibia plate 3, whereas the femoral element is not depicted.

The metal base 2 consists of a horizontal disk 20 secured on one of its faces to an anchoring rod 21 allowing the base 2 to be fixed into the tibia of a patient.

The horizontal disk 20 comprises, on the opposite side to the rod 21, a guide mechanism which utilizes an upstand 22 with an exterior profile in the shape of an arc of a circle. In this case, note that the center of rotation C of the upstand 22 is borne by the tibia bone vertical axis YY'.

The upstand 22 extending vertically above the horizontal disk 20 has a central part 23 integral on each side with two vertical edges 24 and 25 which are not as tall as the central part 23.

In addition, the upstand 22 is positioned on the horizontal disk 20 of the metal base 2 a certain distance away from the center of rotation C.

The tibia plate 3, which is made of plastic, has a flat lower face 30 arranged in a horizontal plane parallel to the plane containing the disk 20 of the metal base 2.

On the opposite side to the face 30 the tibia plate 3 has an upper face 31 with two tracks 32 and 33 of concave profile which are intended to receive the condyles of the femoral element, not depicted.

The lower face 30 is pierced with a housing 34 with the same radius of curvature as the upstand 22 secured to the metal plate 2.

The housing 34 has cutaways 35 and 36 of a larger size which are intended to receive respectively the central part 23 and the lateral edges 24 and 25 of the upstand 22.

It can be seen that the tibia plate 3, and more particularly its lower face 30, is resting on the horizontal disk 20 of the metal base 2, that the upstand 22 enters the housing 34.

The latter has dimensions that exceed those of the upstand 22 so that the tibia plate 3 can slide freely in rotation about the center of rotation C of the upstand 22 in the direction of the arrow F illustrated in FIG. 1.

The upstand 22, which is in the shape of an arc of a circle or curved, is positioned in the anterior part of the metal base 2 and oriented in a substantially medio-lateral direction.

Figure 5:
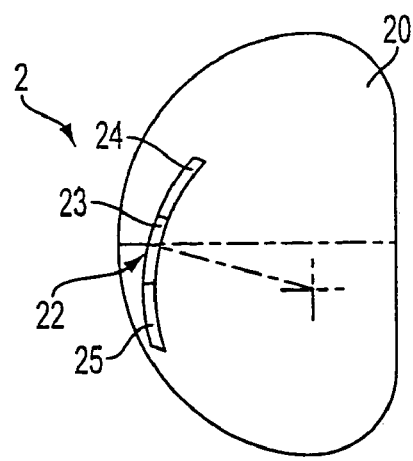

FIGS. 4 and 5 show a first alternative form of the knee prosthesis 1 according to the present invention.

The knee prosthesis 1 is identical to the one described earlier, that is to say that it comprises a metal base 2 and a plastic tibia plate 3.

The metal base 2 has, and this is what differentiates it from the one described above, the position of the guide mechanism on the horizontal disk 20. In effect, the guide mechanism utilizes an upstand 22 in the shape of an arc of a circle and the profile of which is similar to the one described earlier, but the center of rotation C' of which is offset from that C borne by the tibia bone vertical axis YY'.

Note that the center of rotation C' can be positioned anywhere, either on the horizontal disk 20 or off it, while at the same time keeping the guide mechanism on the horizontal disk 20 and more specifically at a particular point.

Just as before, the upstand 22 provided with its central part 23 and its lateral edges 24 and 25 enters the housing 34 formed in the lower face 30 of the plastic tibia plate 3 to allow the latter to slide in rotation over the metal base 2 and about the center of rotation C' in the direction of the arrow F1 in FIG. 4.

The upstand 22, which is in the shape of an arc of a circle or curved, is positioned in the anterior part of the metal base 2 and oriented in a substantially medio-lateral direction.

Figure 6:
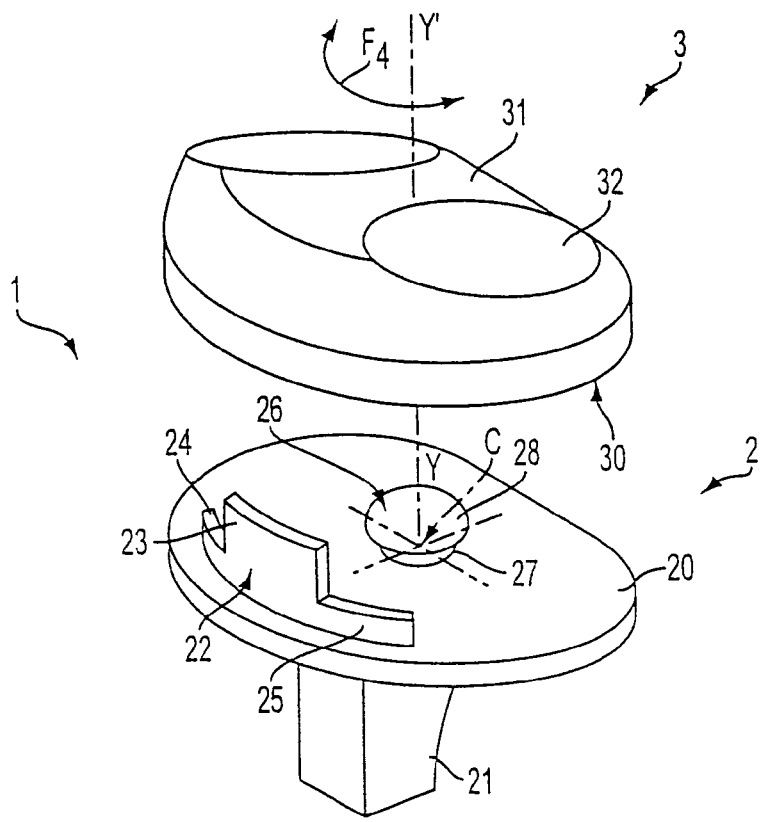
FIGS. 6, 7 and 8 are views showing a second alternative form of the knee prosthesis in which the metal base has, on its axis of rotation, a peg for retaining the plastic tibia plate.
Figure 7:
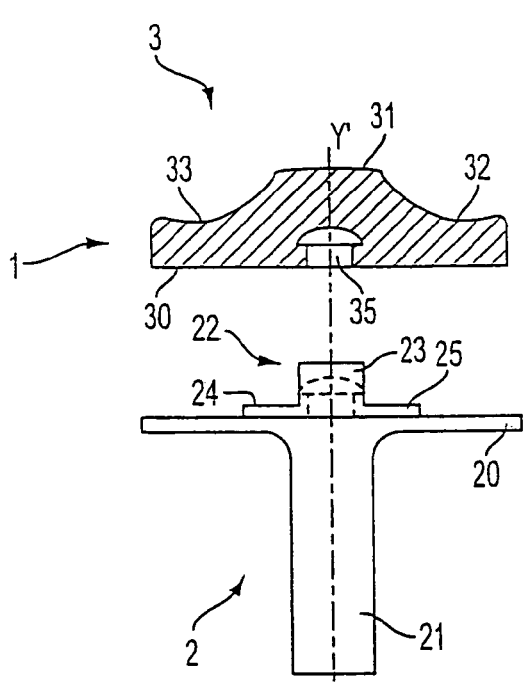
Figure 8:
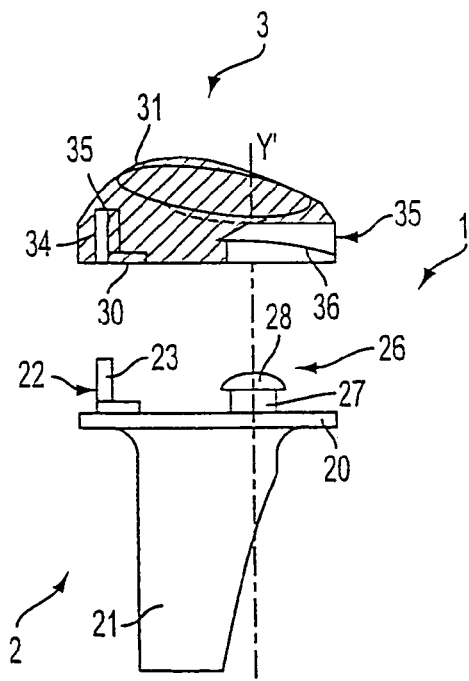

FIGS. 6-8 illustrate a second alternative form of the knee prosthesis 1 according to the present invention.

The knee prosthesis 1 is identical to the one described in FIGS. 1 to 3, namely it comprises a metal base 2 and a plastic tibia plate 3.

The metal base 2 comprises, on its horizontal disk 20, and on the opposite side to its anchoring rod 21, guide mechanism which utilizes the upstand 22 formed from a central part 23 and of two lateral edges 24 and 25.

Furthermore, the horizontal disk 20 comprises, at the center of rotation C of the upstand 22 which is borne by the tibia bone vertical axis YY', a retaining peg 26 extending vertically above the said disk 20.

The retaining peg 26 constitutes a guide means that is in addition to the guide means formed by the upstand 22. Thus, the peg 26 is positioned on the center of rotation C of the tibia plate 3 on the metal base 2.

The retaining peg 26 consists of a cylindrical pin 27 integral with a head 28 whose outside diameter exceeds that of the pin.

The additional guide mechanism or peg 26 is an integral part of the pin 27, 28 to prevent the tibia plate 3 from lifting off the metal base 2 when the prosthesis is in motion.

The tibia plate 3 has, on its lower face 30, the housing 34 that receives the upstand 22 and a cutout 35 with inclined faces 36. When the plate 3 is mounted on the base 2, this cutout engages with the retaining peg 26 so that the head 28 lies above the inclined faces 36.

It can be seen that the retaining peg 26, when it engages with the cutout 35, allows the tibia plate 3 to be prevented from lifting under a tensile force when the plate is sliding in rotation F4 on the metal base 2.

Figure 9:
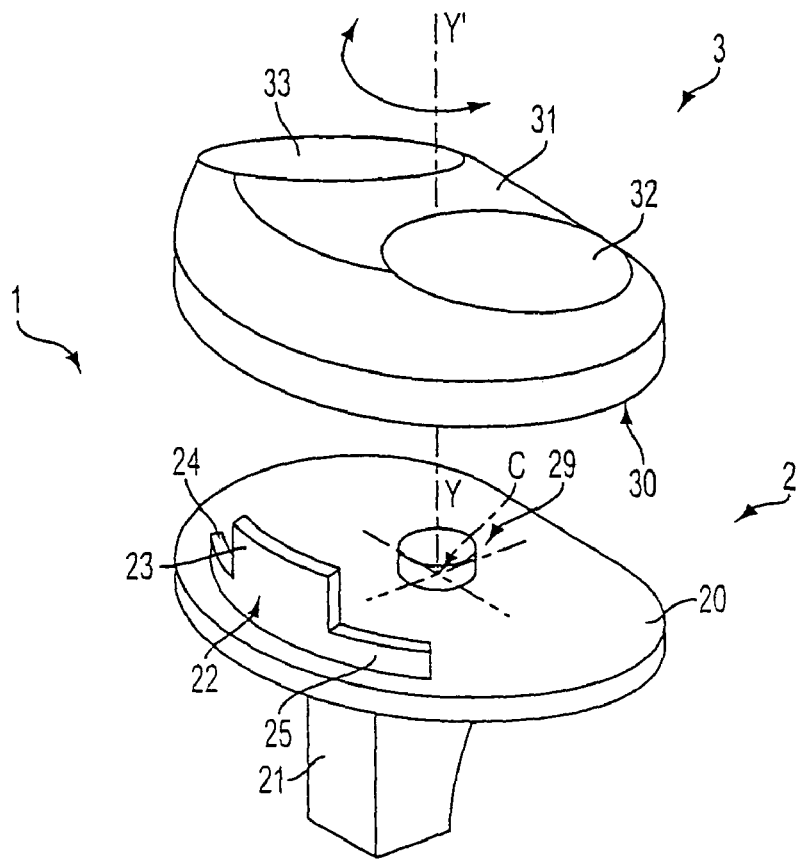
FIGS. 9, 10 and 11 are views showing a third alternative form of the knee prosthesis in which the metal base has, on its axis of rotation, an additional peg for centering the plastic tibia plate.
Figures 10, 11:
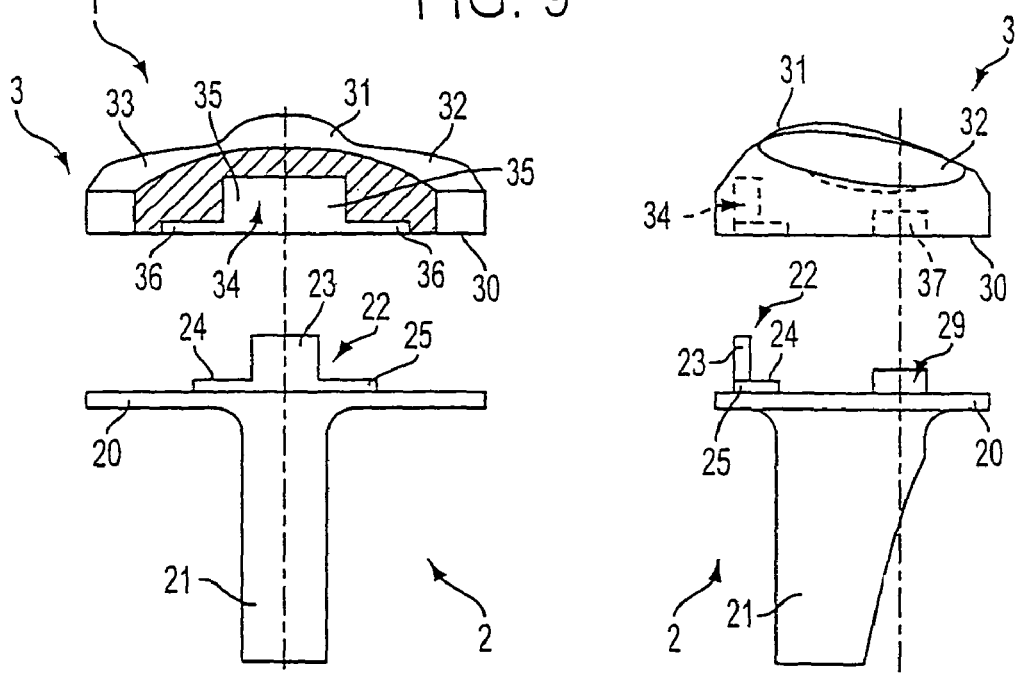

FIGS. 9 to 11 show a third alternative form of the knee prosthesis 1 according to the invention.

Thus, the metal base 2 comprises, opposite the upstand 22, and in the region of the center of rotation C which is borne by the tibia bone vertical axis YY', a centering peg 29 extending vertically above the horizontal disk 20.

The centering peg 29 extends vertically above the horizontal disk 20 by a short height, constituting a guide mechanism that is in addition to the guide mechanism formed by the upstand 22.

The centering peg 29 consists of a short cylindrical pin.

The plastic tibia plate 3 comprises, on its lower face 30 and opposite the housing 34, a blind hole 37 intended to receive the centering peg 29 when the plate is fitted onto the metal base 2.

The centering peg 29 provides a physical embodiment of the center of rotation C of the upstand 22 as the tibia plate 3 slides in rotation over the metal base 2.

Figure 12:
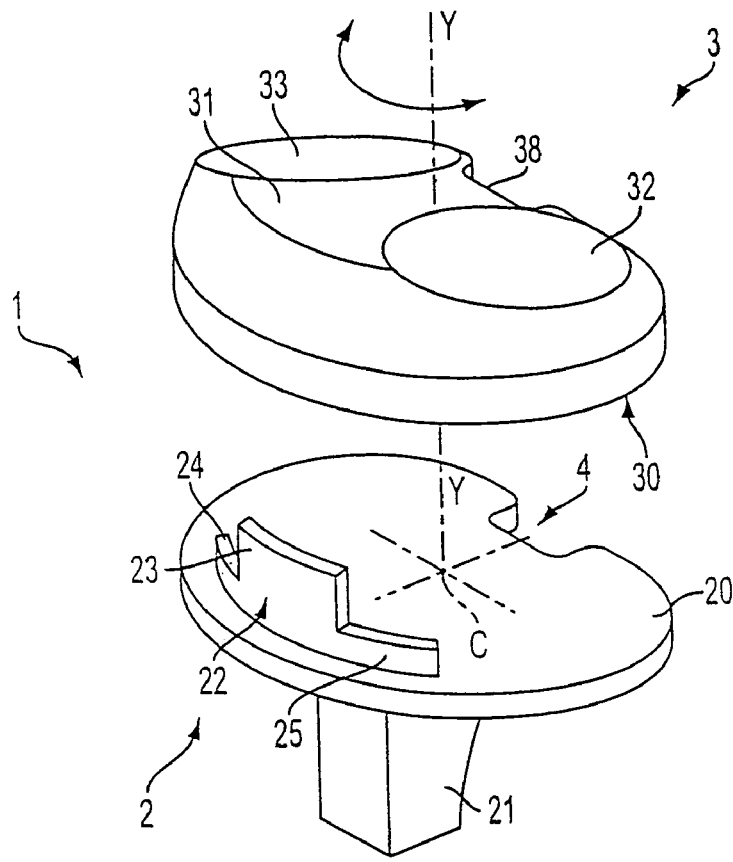
FIGS. 12, 13 and 14 are views depicting a fourth alternative form of the knee prosthesis which has a cutout through which the posterior cruciate ligament can pass.
Figures 13, 14:
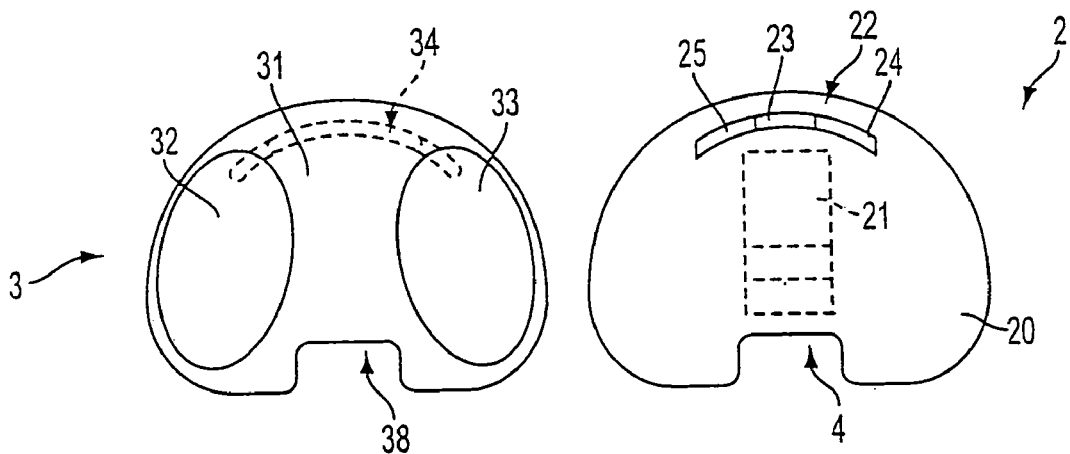

The knee prosthesis 1 illustrated in FIGS. 12 to 14 differs from the one shown in FIGS. 1 to 3 only in the fact that the metal base 2 and the plastic tibia plate 3 respectively comprise a cutout 4 and 38 for the passage of the posterior cruciate ligament.

Quite obviously, the prosthesis 1 shown in FIGS. 12 to 14 works in the same way as the one described in FIGS. 1 to 3.

Figure 15:
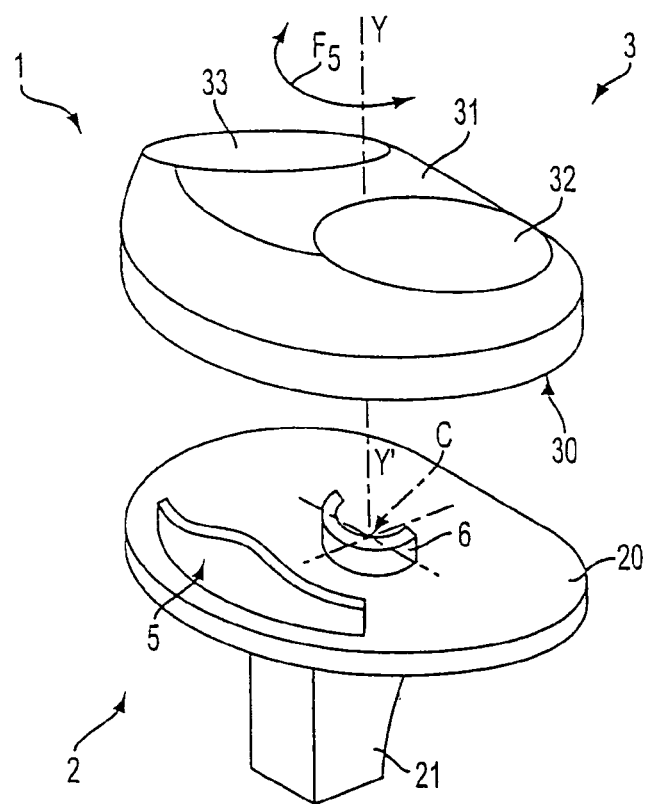
FIGS. 15 to 21 are views illustrating alternative forms of the knee prosthesis in which the metal base has two opposed guide upstands but one of which is borne by the center of rotation of the second.

FIG. 15 shows the knee prosthesis 1 equipped with its metal base 2 and with its tibia plate 3. The metal base 2 comprises, on its horizontal disk 20, and more specifically on the opposite side to the anchoring rod 21, an upstand 5 in the shape of an arc of a circle and of variable height. This upstand has a profile which differs from those that make up the upstands described earlier. At the center of rotation C of the upstand 5 there is a second upstand 6 in the shape of an arc of a circle.

The upstands 5 and 6 engage in housings, not depicted, but formed on the face 30 of the tibia plate 3 to allow the plate to be guided as it slides in rotation about the center of rotation C, as depicted by the arrow F5.

The upstand 5, in the shape of an arc of a circle or curved, is positioned in the anterior part of the metal base 2 and oriented in a substantially medio-lateral direction.

The upstand 6 constitutes a guide mechanism that is in addition to the guide mechanism formed by the upstand 5. Thus, the upstand 6 is positioned on the center of rotation C of the tibia plate 3 on the metal base 2.

Provision may be made for the center of rotation of the upstands 5 and 6 to be offset from the tibia bone vertical axis YY' without this in any way altering the subject of the invention.

Figure 16:
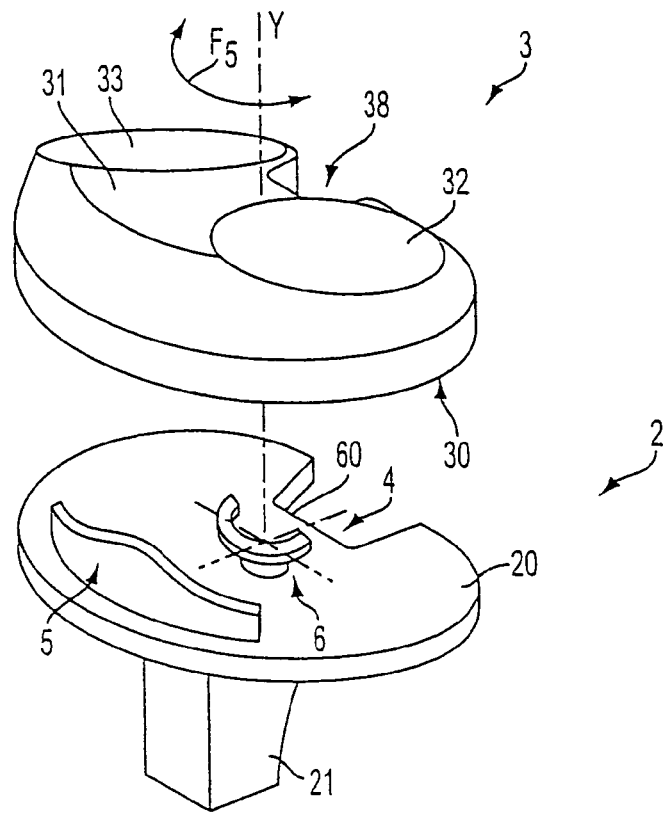
Figures 17, 18:
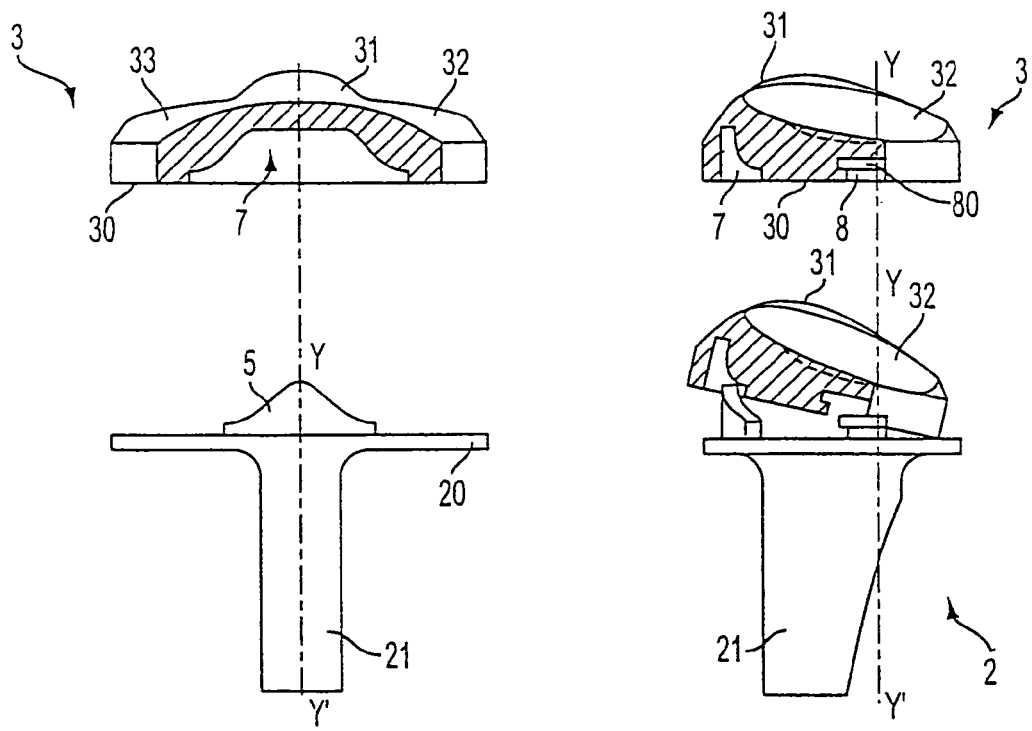

FIGS. 16 to 18 depict an alternative form of the knee prosthesis 1 shown in FIG. 15, namely wherein the upstand 6 is integral with a flange 60 forming a kind of small plate set out in a horizontal plane parallel to the plane containing the disk 20 of the metal base 2.

The tibia plate 3 has, on its face 30, housings 7 and 8 intended to receive respectively the upstands 5 and 6 to allow the tibia plate 3 to slide in rotation over the metal base 2 above the center of rotation C and in the direction of the arrow F5.

The housing 7 has a profile essentially identical to that of the upstand 5, and at the very least, in the shape of an arc of a circle for guiding the tibia plate 3 in its travel.

The housing 8 has a profile essentially identical to the flange 60 of the additional guide mechanism or upstand 6 for guiding the tibia plate 3 in its travel.

The housing 8 is pierced with an internal slot 80 intended to receive the flange 60 of the upstand 6 to achieve a kind of snap-fastening of the tibia plate 3 to the base 2, so that the plate cannot lift under a tensile force.

Note that the upstands 5 and 6 in the shape of an arc of a circle are curved in the same direction and about the same center of rotation C or C' when the latter is offset from the tibia bone vertical axis YY'.

As in FIG. 12, the metal base 2 and the tibia plate 3 may respectively comprise cutouts 4 and 38 for the passage of the posterior cruciate ligament.

Figure 19:
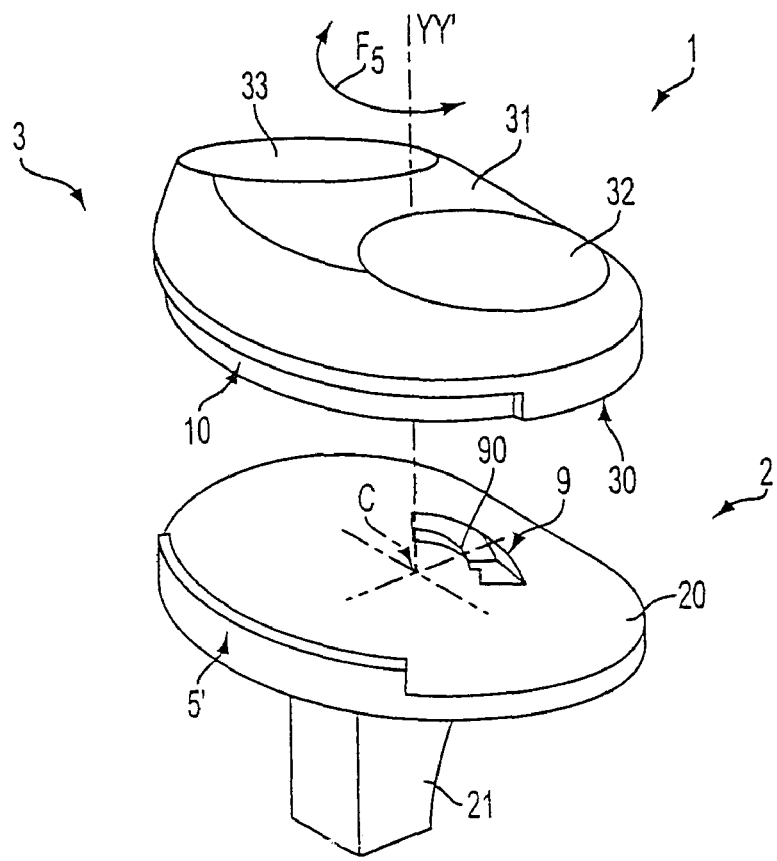
Figure 20:
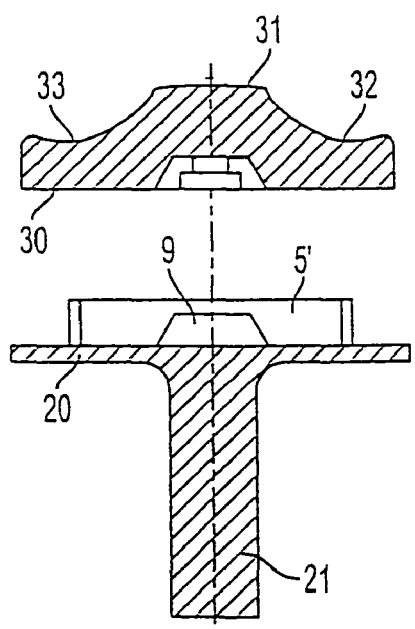
Figure 21:
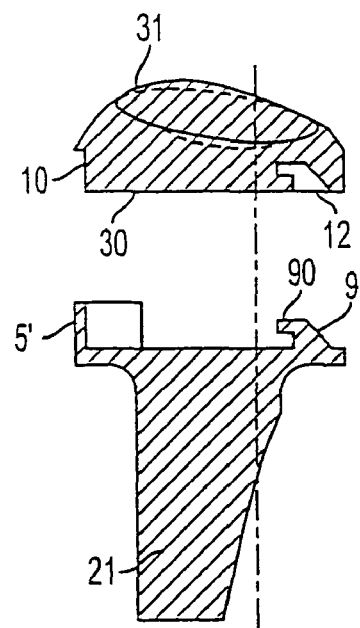

In FIGS. 19 to 21 the knee prosthesis 1 comprises, on its metal base 2, a first upstand 5' set out at the external periphery of the horizontal disk 20. Opposite the upstand 5' the horizontal disk 20 is secured to another upstand 9 in the shape of an arc of a circle, but the radius of curvature of which is inverted compared with that of the upstand 5'.

The upstand 5, which is in the shape of an arc of a circle or curved, is positioned in the anterior part of the metal base 2 and oriented in a substantially medio-lateral direction.

The upstand 9 constitutes a guide mechanism that is in addition to the guide mechanism formed by the upstand 5'. Thus, the upstand 9 is positioned on the center of rotation C of the tibia plate 3 on the metal base 2.

The upstand 9 has the same center of rotation C as the upstand 5', but the center may be offset, depending on the configuration of the knee prosthesis, from the tibia bone vertical axis YY'.

The upstand 9 is integral with a flange 90, the function of which will be seen more clearly later.

The tibia plate 3 has, on its lower periphery, that is to say the one that lies between the faces 30 and 31, a recess 10 receiving the upstand 5' when the tibia plate 3 is fitted onto the metal base 2.

On the opposite side to the recess 10, the lower face 30 is pierced with a housing 12 into which the upstand 9 can be snap-fastened to, on the one hand, guide the plate 3 as it slides in rotation about its center C, and, on the other hand, retain the plate to prevent it from lifting off the metal base 2.

Figure 22:
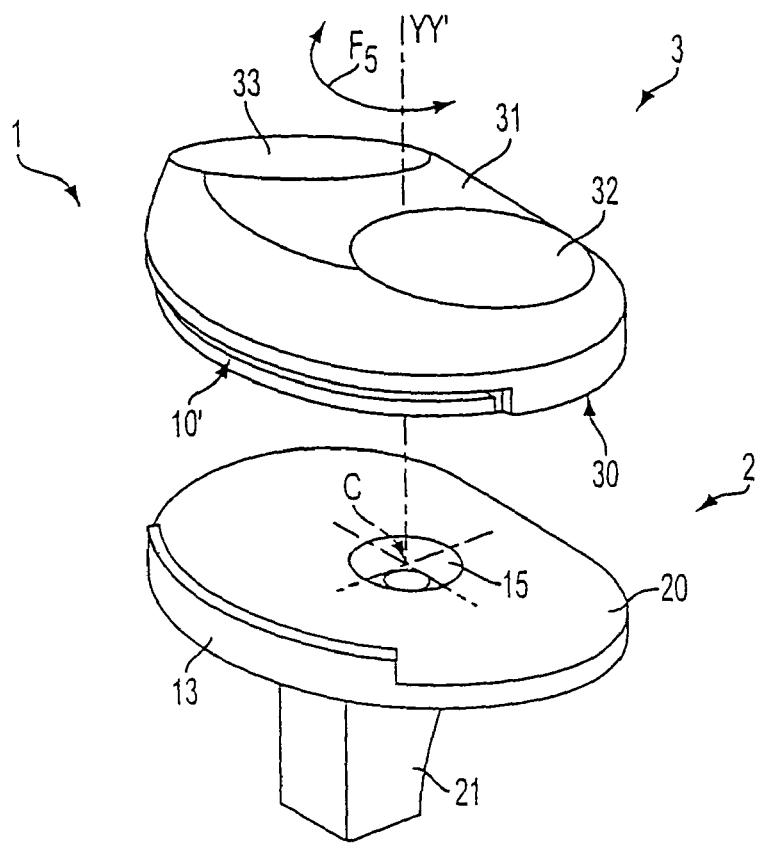
FIGS. 22 to 24 are views depicting other alternative forms of the knee prosthesis according to the present invention.
Figure 23:
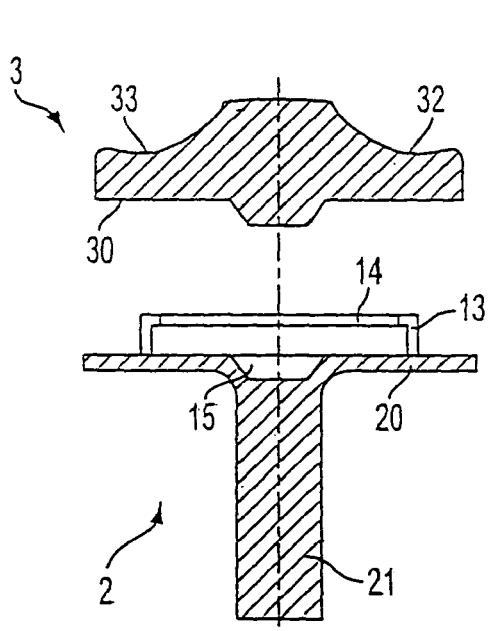
Figure 24:
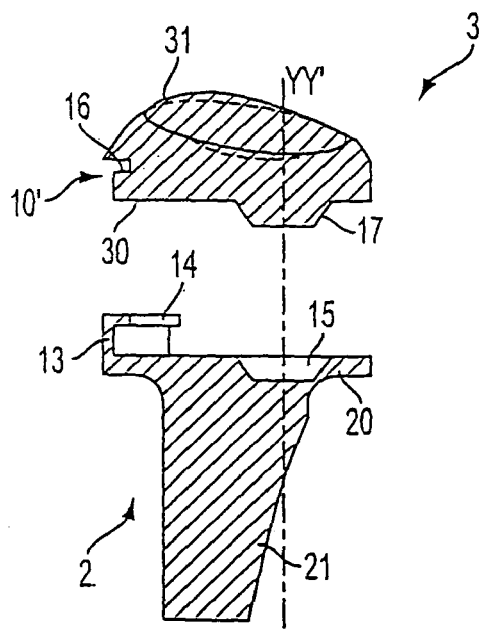

In FIGS. 22 to 24 the knee prosthesis 1 comprises the metal base 2, the horizontal disk 20 of which has, on its external periphery, an upstand 13 in the shape of an arc of a circle integral with a flange 14 directed toward the tibia bone vertical axis YY'.

The horizontal disk 20 is pierced at the center of rotation C of the upstand 13 with a dish-shaped housing 15 which constitutes a guide mechanism that is in addition to the guide mechanism formed by the upstand 13. This upstand, which is in the shape of an arc of a circle or curved, is positioned in the anterior part of the metal base 2 and oriented in a substantially medio-lateral direction.

The upstand 13 and the housing 15 may comprise a center of rotation C which is offset from the tibia bone vertical axis YY'.

On its external periphery and between the faces 30 and 31, the tibia plate 3 has a recess 10' in which there is formed a horizontal slot 16 intended to receive the flange 14 of the upstand 13 as the plate 3 slides in rotation over the metal base 2.

The lower face 30 is integral with as stub 17 with a conical tapering profile capable of engaging with the housing 15 formed in the horizontal disk 20 of the metal base 2.

The upstand 13 equipped with its flange 14, the housing 15, the recess 10' and its slot 16, and the stub 17 constitutes the mechanism of guiding the tibia plate 3 over the metal base 2 as the plate slides in rotation in the direction of the arrow F5.

Figures 25, 26:
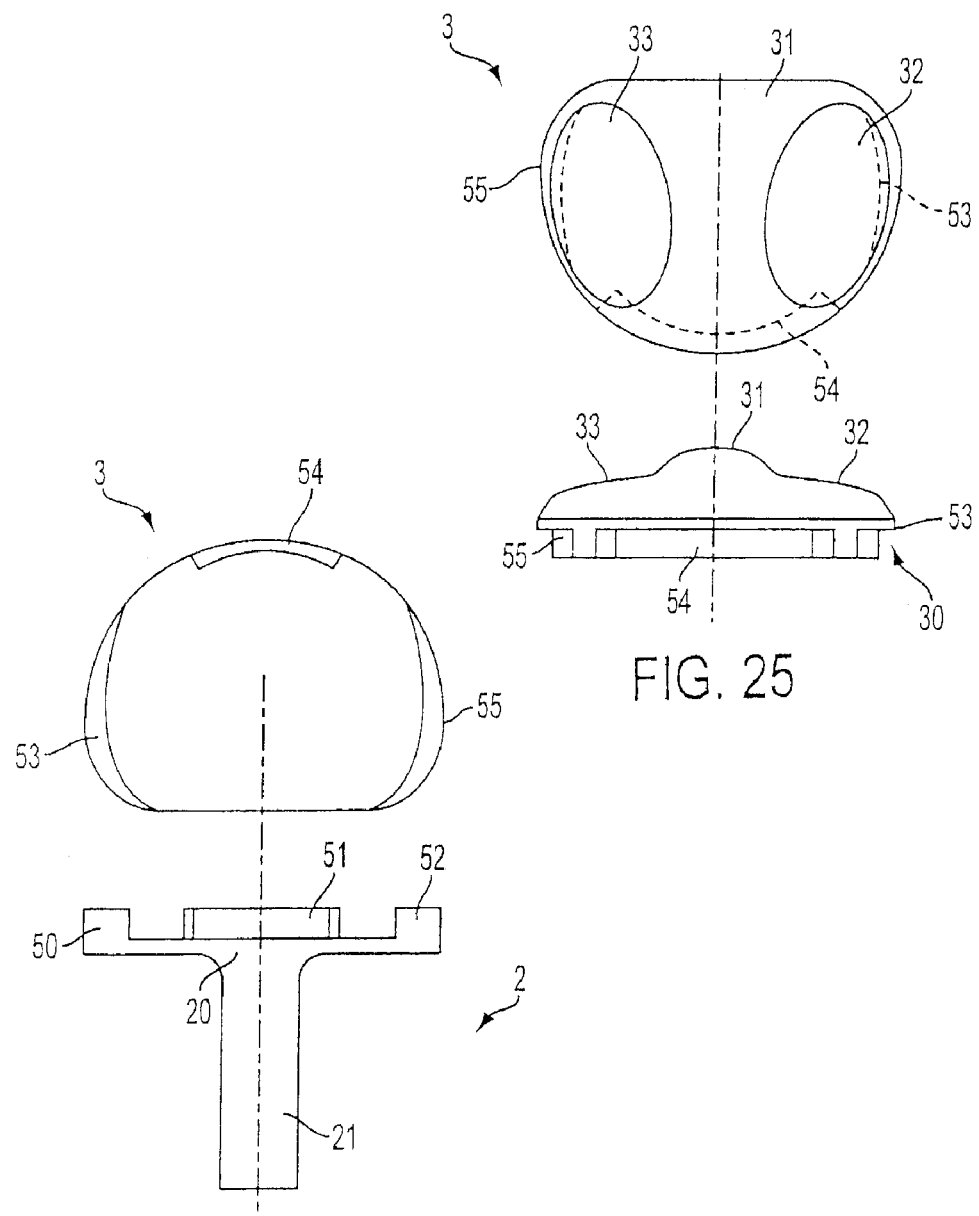
FIGS. 25 and 26 are views illustrating a guide mechanism set out at the periphery of the metal base and of the tibia plate of the knee prosthesis.

In FIGS. 25 and 26, the metal base 2 of the knee prosthesis 1 comprises, on its horizontal disk 20, three peripheral upstands 50, 51 and 52 extending vertically above the horizontal disk 20.

The tibia plate 3 comprises, on its external periphery, three peripheral recesses 53, 54 and 55 which are intended to receive the upstands 50, 51 and 52 respectively to allow the plate to be guided as it slides in rotation about the center of rotation of the upstands, which is identical for all three.

The upstand 51, which is the shape of an arc of a circle or curved, is positioned in the anterior part of the metal base 2 and oriented in a substantially medio-lateral direction.

The upstands 50, 52 in the shape of an arc of a circle constitute guide mechanism which are in addition to the guide mechanism formed by the upstand 51. The upstands 50, 52 are positioned near the center of rotation C of the tibia plate 3 on the metal base 2.

Figure 27:
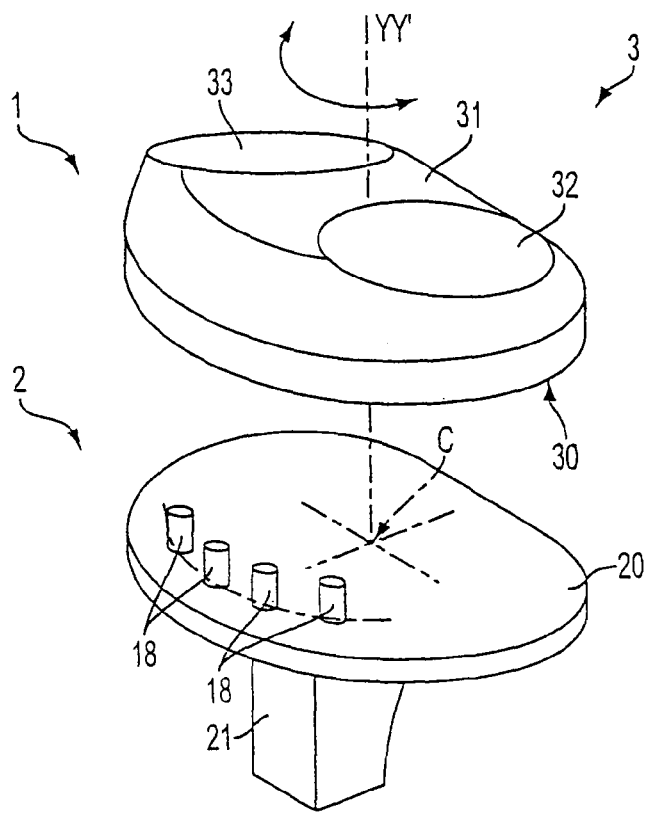
FIGS. 27 to 29 are views showing a guide mechanism utilizing at least two vertical pegs integral with the metal base and which engage with a housing formed in the tibia plate.
Figures 28, 29:
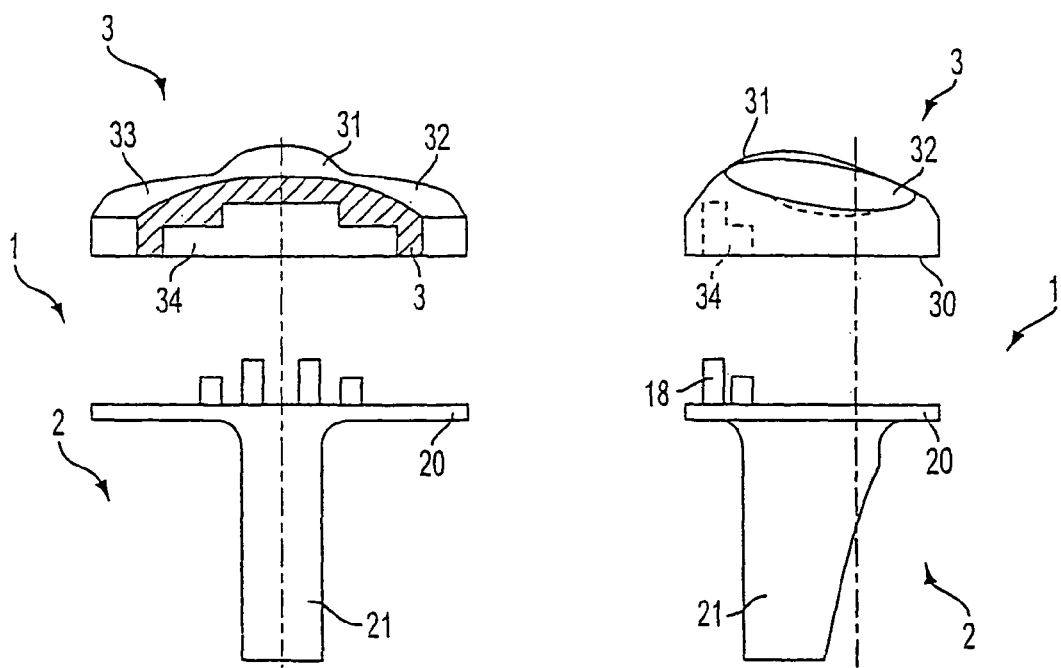

In FIGS. 27 to 29, the metal base 2 of the knee prosthesis 1 comprises, on its horizontal disk 20, vertical page 18 set out in an arc of a circle about a center of rotation C which may be either borne by or offset from the tibia bone vertical axis YY'.

The pegs 18 set out in an arc of a circle are positioned in the anterior part of the metal base 2 and oriented in a substantially medio-lateral direction.

In this example, the tibia plate 3 is identical to the one described in FIGS. 1 to 3, that is to say that its lower face 30 has a housing 34 intended to receive the pegs 18 for guiding the plate as it slides in rotation with respect to the metal base 2.

It can be seen that in each example described hereinabove it is possible, as the case may be, for the center of rotation of the upstands or of the pegs either to be offset or not to be offset in order to determine a particular rotational sliding of the tibia plate 3 with respect to the metal base 2.

Note too that in each example described hereinabove, cutouts 4 and 38 may or may not be provided for the passage of the posterior cruciate ligament.

Furthermore, it can be seen that the guide mechanism in each example described hereinabove are positioned a certain distance away from the center of rotation C, C'.

It will be observed that the short height of the upstand or of the pegs, and its anterior position on the metal base 2 allows the plastic plate 3 to be fitted onto the base easily using a strictly anterior approach, the plate requiring upward clearance only by the height of the upstand or of the pegs as shown in FIG. 21.

It will furthermore be observed that the plastic plate 3 cannot slide in rotation over the metal base 2 except within the limits set by the difference in dimensions between the housing and the corresponding upstand or pegs, and this prevents any undesired excess movement.

This being so, it will be readily understood that a plastic plate 3 can be obtained in which the dimensions of the housing are identical to those of the upstand or of the corresponding pegs, so as to prevent any travel of the plate over the metal 2. This allows the surgeon, according to the particular surgical case, to return to a knee prosthesis system with plastic plate which is fixed to the metal base 2, without having to change the latter.

We claim:

1. A knee prosthesis comprising:
   a metal base having upper and lower surfaces,
   an anchoring rod extending from said lower surface for fixing said base into a tibia of a patient,
   a plastic tibial plate having a lower surface for engaging said upper surface of said base, said upper surface of said base including
      an anterior portion spaced radially ahead of a tibia bone axis (Y,Y') when the anchoring rod is fitted into the tibia of the patient,
      an arcuately oriented guide structure for controlling any relative rotation of said plate and said base, said arcuately oriented guide structure defining an arc of a circle having a center of rotation (C,C') about which said plate may rotate, said guide structure being positioned in the anterior portion of the upper surface of said base and extending upwardly from this anterior portion, and being oriented, along its arc, in a substantially medio-lateral direction and extending, along its arc, on both sides of a median plane of the base parallel to a sagittal plane of the patient and containing the tibia bone axis (Y,Y') when said anchoring rod is fitted into the tibia of the patient, and
   a recess in said lower surface of said plate of an arcuate shape for cooperatively receiving said guide structure of said base such that any relative rotation between said plate and said base is determined by an arcuate length of said recess relative to an effective arcuate length of said guide structure,
   wherein said guide structure includes an upstand in the shape of the arc of a circle, wherein said upstand includes a central portion and two opposite side portions that extend from each medio-lateral side of the central portion and wherein said central portion extends upwardly from said upper surface of said base at a greater distance than said side portions.

2. The knee prosthesis of claim 1 wherein said plate includes a peripheral edge, said recess being formed along said peripheral edge, and wherein said anterior portion of said upper surface of said base extends to a peripheral edge of said base and said upstand extends from said peripheral edge of said base.

3. The knee prosthesis of claim 2 in which said upstand includes an arcuate retaining flange which extends toward the center of rotation (C,C') and is receivable within a horizontal slot formed in said periphery of said plate.

4. The knee prosthesis of claim 1 in which the center of rotation (C) is generally aligned with the tibial bone vertical axis (Y,Y') when said anchoring rod is fitted into the tibia of the patient.

5. The knee prosthesis of claim 1 wherein the center of rotation (C') is offset with respect to the tibial bone vertical axis (Y,Y') when said anchoring rod is fitted into the tibia of the patient.

6. The knee prosthesis of claim 1 further including a centering element of cylindrical profile extending upwardly from said upper surface of said base so as to be coaxial with the center of rotation (C,C').

7. The knee prosthesis of claim 1 including a retaining member mounted to said base and which is cooperatively receivable within an opening in said plate for preventing said plate from being lifted from engagement from said base when mounted thereto.

8. The knee prosthesis of claim 7 wherein said retaining member includes a cylindrical pin extending from said upper surface of said base and axially aligned with the center of rotation (C,C') on the base, said pin including an integral head having a peripherally extending edge, and said opening including a cutout for receiving a portion of said peripherally extending edge of said head.

9. The knee prosthesis of claim 7, wherein the upstand is a first upstand, and wherein said retaining member includes a second upstand that is a retaining upstand in the configuration of an arc of a circle having a central axis at the center of rotation (C,C') of said plate, and wherein said retaining upstand includes a peripheral arcuate flange of a configuration to snap fit within a slot formed in the opening of said plate.

10. The knee prosthesis of claim 7, wherein the upstand is a first upstand, and wherein said retaining member includes a second upstand that is a retaining upstand in the shape of an arc of a circle curved in a direction opposite to the arc defined by said first upstand, said retaining upstand being positioned so as to have a axis of rotation at the axis of rotation (C,C'), and said retaining upstand including a peripheral arcuate flange of a configuration to snap fit with a slot formed in the opening of said plate.

11. The knee prosthesis of claim 7, wherein the upstand is a retaining upstand in the configuration of an arc of a circle having a central axis at the center of rotation (C,C') of said plate, and wherein said retaining upstand includes a peripheral arcuate flange of a configuration to snap fit within a slot formed in the opening of said plate.

12. The knee prosthesis of claim 1 wherein each of said base and said plate include cutouts through which a posterior cruciate ligament may pass.

13. The knee prosthesis of claim 1 wherein said plate includes a peripheral edge, said recess being formed along said peripheral edge of said plate, and the anterior portion of said upper surface of said base extends to a peripheral edge of said base.

14. The knee prosthesis of claim 13 wherein said guide structure includes an arcuate retaining flange that extends toward the center of rotation (C,C') and is receivable within a horizontal slot formed in said peripheral edge of said plate.

15. A method of implantation of a knee prosthesis, the knee prosthesis comprising:
   a metal base having upper and lower surfaces, an anchoring rod extending from the lower surface of the base for fixing the base into a tibia of a patient, the upper surface of the base including an anterior portion spaced radially ahead of a tibia bone axis (Y,Y') when the anchoring rod is fitted into the tibia of the patient,
   a plastic tibial plate having a lower surface for engaging the upper surface of the base,
   an arcuately oriented guide structure for controlling any relative rotation of the plate and the base, said arcuately oriented guide structure defining an arc having a center of rotation (C or C') about which the plate may rotate on the base for controlling any relative rotation of the plate and the base,
   the guide structure being positioned in the anterior portion of the upper surface of the base and extending upwardly from this anterior portion, and being oriented, along its arc, in a substantially medio-lateral direction and extending, along its arc, on both sides of a median plane of the base parallel to a sagittal plane of the patient and containing the tibia bone axis (Y,Y') when the anchoring rod is fitted into the tibia of the patient, and a recess in the lower surface of the plate of an arcuate shape for cooperatively receiving the guide structure of the base such that any relative rotation between the plate and the base is determined by an arcuate length of the recess relative to an effective arcuate length of the guide structure;

the method including a step of fitting of the plate on the base by a strictly anterior surgical approach, wherein, before fitting the plate on the base, the plate is surgically cleared upwardly only by a height of the guide structure.

16. A knee prosthesis comprising:

a metal base having upper and lower surfaces, an anchoring rod extending from said lower surface for fixing said base into a tibia of a patient, a plastic tibial plate having a lower surface for engaging said upper surface of said base, said upper surface of said base including an anterior portion spaced radially ahead of a tibia bone axis (Y,Y') when the anchoring rod is fitted into the tibia of the patient, an arcuately oriented guide structure for controlling any relative rotation of said plate and said base, said arcuately oriented guide structure defining an arc of a circle having a center of rotation (C,C') about which said plate may rotate, said guide structure being positioned in the anterior portion of the upper surface of said base and extending upwardly from this anterior portion, and being oriented, along its arc, in a substantially medio-lateral direction and extending, along its arc, continuously on both sides of a median plane of the base parallel to a sagittal plane of the patient and containing the tibia bone axis (Y,Y') when said anchoring rod is fitted into the tibia of the patient, and a recess in said lower surface of said plate of an arcuate shape for cooperatively receiving said guide structure of said base such that any relative rotation between said plate and said base is determined by an arcuate length of said recess relative to an effective arcuate length of said guide structure, wherein said guide structure includes an upstand in the shape of the arc of a circle, wherein said upstand extends from said base, wherein said upstand includes a central portion and two opposite side portions that extend from each medio-lateral side of the central portion and wherein said central portion extends upwardly from said upper surface of said base at a greater distance than said side portions.

17. A knee prosthesis comprising:

a metal base having upper and lower surfaces, an anchoring rod extending from said lower surface for fixing said base into a tibia of a patient, a plastic tibial plate having a lower surface for engaging said upper surface of said base, said upper surface of said base including an anterior portion spaced radially ahead of a tibia bone axis (Y,Y') when the anchoring rod is fitted into the tibia of the patient, an arcuately oriented guide structure for controlling any relative rotation of said plate and said base, said arcuately oriented guide structure defining an arc of a circle having a center of rotation (C,C') about which said plate may rotate, said guide structure being positioned in the anterior portion of the upper surface of said base and extending upwardly from this anterior portion, and being oriented, along its arc, in a substantially medio-lateral direction and extending, along its arc, continuously on both sides of a median plane of the base parallel to a sagittal plane of the patient and containing the tibia bone axis (Y,Y') when said anchoring rod is fitted into the tibia of the patient, and a recess in said lower surface of said plate of an arcuate shape for cooperatively receiving said guide structure of said base such that any relative rotation between said plate and said base is determined by an arcuate length of said recess relative to an effective arcuate length of said guide structure, a centering element of cylindrical profile extending upwardly from said upper surface of said base so as to be coaxial with the center of rotation (C,C');

wherein said guide structure includes an upstand in the shape of the arc of a circle, wherein said upstand extends from said base.

* * * * *